United States Patent [19]

Maeda et al.

[11] Patent Number: 4,590,184

[45] Date of Patent: May 20, 1986

[54] ANTIOSTEOPOROTIC PHARMACEUTICAL COMPOSITION CONTAINING 24,25-DIHYDROXYCHOLECALCIFEROL AS AN ACTIVE INGREDIENT

[75] Inventors: Yuji Maeda, Nagareyama; Hideyuki Yamato, Tokyo; Takayoshi Fujii, Tokyo; Yasuhiko Kobayashi, Tokyo; Kenichi Saito, Tokyo; Tadaaki Kato, Tokyo; Chikao Yoshikumi, Kunitachi, all of Japan

[73] Assignee: Kureha Kagaku Kogyo Kabushiki Kaisha, Tokyo, Japan

[21] Appl. No.: 662,044

[22] Filed: Oct. 18, 1984

[30] Foreign Application Priority Data

Oct. 24, 1983 [JP] Japan .................................. 58-198454

[51] Int. Cl.$^4$ ............................................ A61K 31/59

[52] U.S. Cl. .................................. 514/167; 260/397.2

[58] Field of Search ..................... 424/236; 260/397.2; 514/167

[56] References Cited

U.S. PATENT DOCUMENTS 3,715,374 2/1973 DeLuca et al. .................. 260/397.2
4,338,250 7/1982 DeLuca et al. .................. 260/397.2
4,456,553 6/1984 Oshida et al. .................... 260/397.2

Primary Examiner—Elbert L. Roberts
Attorney, Agent, or Firm—Cushman, Darby & Cushman

[57] ABSTRACT

Disclosed herein is a pharmaceutical composition in dosage unit form, which comprises a dosage effective for treating osteoporosis of a compound of 24,25-dihydroxycholecalciferol and a pharmaceutically acceptable carrier.

2 Claims, 3 Drawing Figures (×40)

(×40)

(x 40)

ANTIOSTEOPOROTIC PHARMACEUTICAL COMPOSITION CONTAINING 24,25-DIHYDROXYCHOLECALCIFEROL AS AN ACTIVE INGREDIENT

SUMMARY OF THE INVENTION

In a first aspect of the present invention, there is provided a pharmaceutical composition in dosage unit form, which comprises a dosage effective for the treatment of osteoporosis of a compound of 24,25-dihydroxycholecalciferol (hereinafter referred to the present substance) and a pharmaceutically acceptable carrier.

In a second aspect of the present invention, there is provided a method for treating osteoporosis, which comprises administering to a patient suffering from osteoporosis an effective amount of a compound of 24,25-dihydroxycholecalciferol.

BACKGROUND OF THE INVENTION

The present invention relates to a pharmaceutical composition for treating osteoporosis, which contains a compound of 24,25-dihydroxycholecalciferol as an active ingredient.

In recent years, the average life span of the Japanese has rapidly extended, and accordingly the population of people of age of more than 65 is now more than ten millions. Consequently, the population of the patients treated as those suffering from osteoporosis is presumed to be as many as 3 millions.

Accordingly, the elucidation of the morbid state and the establishment of the therapy of osteoporosis are very important problems, and the development of the safe medicine for treating osteoporosis has been keenly expected.

Although it is considered that the occurrence of osteoporosis is due to several causes such as endocrinical causes, nutritive causes, physical causes, hereditary causes, etc., cases of postmenopausal osteoporosis occupies the largest percentage of all the cases of osteoporosis.

An activated vitamin $D_3$, for instance, $1\alpha$-hydoroxycholecalciferol or $1\alpha,25$-dihydroxycholecalciferol, is used as an active ingredient of the pharmaceutical composition for treating osteoporosis and the activated vitamin $D_3$ is chemically similar to the present substance, however, there is a side-effect problem in the administration of such an activated vitamin $D_3$ and accordingly, it is necessary to pay a close attention in administering such an activated vitamin $D_3$.

In addition, although the effect of the activated vitamin $D_3$ on the bones of the patient administered therewith is determined by the extent of promotion of absorption of calcium via the intestinal tracts of the patient, such a determination is an indirect determination and it has not been elucidated that there is any direct interrelationship between the extent of promotion of absorption of calcium and the lesion of the bone due to osteoporosis.

In consideration of the above-mentioned situation, the present inventors have studied for the substance utilizable for treating osteoporosis, particularly among the safe and endogenous substances present in healthy human body while examining the antiosteoporotic activity, thereof and as a result, the present inventors have found out that the compounds of 24,25-dihydroxycholecalciferol (hereinafter abbreviated and referred to as 24,25-$(OH)_2$-$D_3$, or more simply as the present substance) have an activity of directly improving the lesion of bones due to osteoporosis to a remarkable extent without exhibiting any side-effects and toxicity, and have attained the present invention.

Osteoporosis referred to in the present invention includes not only senile osteoporosis and postmenopausal osteoporosis but also secondary osteomalacial osteoporosis accompanying osteomalacia, secondary osteoporosis accompanying functional accentuation of the accessory thyroid and topical osteoporosis and abnormal bone both due to articular rheumatism.

BRIEF EXPLANATION OF DRAWINGS

Of the attached drawings.

DETAILED DESCRIPTION OF THE INVENTION

Figure 1:
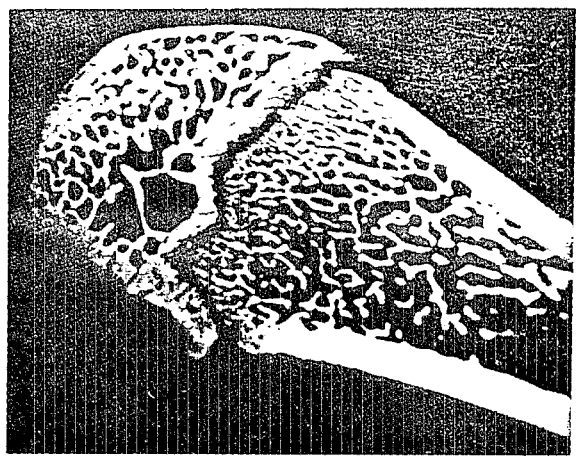
FIG. 1 is the contact microradiograph of the right tibia of a rat in the fifth group (subjected to SHAM and only MCT was administered)

The present substance represented by the formula:

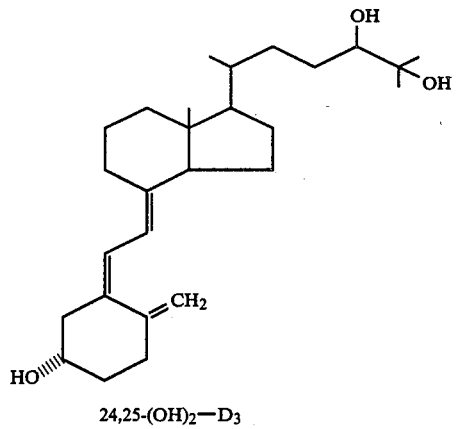

24,25-$(OH)_2$—$D_3$ includes the following two known compounds, 24R,25-dihydroxychdecalciferol and 24S,25-dihydroxycholecalciferol (hereinafter referred to as 24R,25-$(OH)_2$-$D_3$ and 24S,25-$(OH)_2$-$D_3$, respectively), disclosed, for instance, in "Pharmacia", 10, 319–322.

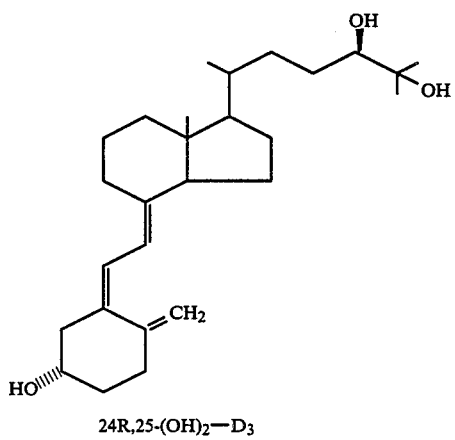

24R,25-$(OH)_2$—$D_3$

-continued

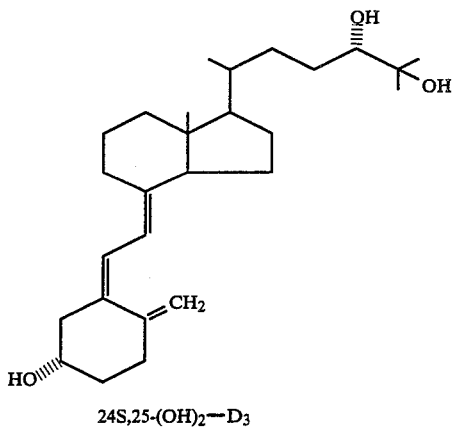

24S,25-(OH)$_2$—D$_3$

Namely, the present substance may be either of the above-mentioned two compounds, and further, may be any mixture thereof, however, more preferable compound is 24R,25-(OH)$_2$-D$_3$.

The antiosteoporotic pharmaceutical composition containing the present substance as an active ingredient may be used in the following various states of formulation via a parenteral route, for instance, intraperitoneal administration, and may be orally administrated.

As the state of formulation of the pharmaceutical composition containing the present substance as an active ingredient, tablet, powder, granule, suppository, capsule, solution in ethanol, solution in oily substance and aqueous suspension may be mentioned for administration. As the oily substance, triglycerides of medium fatty acids, corn oil, cotton seed oil, peanut oil, fish-liver oil, cacao oil, glycerol and oily esters are preferably used. As the other component, lactose, starch, talc, magnesium stearate, sorbic acid, salts of sorbic acid, sugars or derivatives thereof, ethanol, aqueous physiological saline solution, surfactants, antioxidants may be used in combination with the present substance.

The content of the present substance in a dosage unit of a pharmaceutical composition may be 0.00002 to 4% by weight, preferably 0.0002 to 1% by weight, and the daily dose of the present substance for an adult is 0.1 to 100,000 micrograms, preferably 0.5 to 10,000 micrograms.

The acute mammalian toxicity of the present substance is shown as a result of the following animal experiment.

Acute mammalian toxicity test

A solution prepared by dissolving the present substance, 24R,25-(OH)$_2$-D$_3$ or 24S,25-(OH)$_2$-D$_3$, in ethanol, and dissolving the thus formed ethanolic solution into triglyceride of C$_8$ to C$_{10}$-fatty acid so that the concentration of ethanol in the thus formed oily solution is 2% by weight was orally administered to each of 10 male ICR mice of body weight of 25±3 g at a dose rate of 150 mg/kg. After finding no symptoms of intoxication due to the administration on each of the thus treated mice for 2 weeks of observation after administration, the mice were butchered to carry out autopsy, blood-biochemical examination and histopathological examination. The thus obtained informations were quite the same as those obtained on the mice administered only with triglyceride of C$_8$ to C$_{10}$-fatty acid containing 2% by weight of ethanol.

Accordingly, LD$_{50}$(p.o.) of the present substance is larger than 150 mg/kg and the present substance is quite safe for administration.

The present invention will be explained more in detail while referring to the following non-limitative examples.

In addition, the confirmation of the structure of the optical isomer, 24R,25-(OH)$_3$-D$_3$, used in Examples, was carried out following the disclosure in "Tetrahedron Letters", No. 26, 2203–2206 (1975).

EXAMPLE 1

Test for antiosteoporotic activity of the present substance

After one week of acclimatization of sixty female Sprague-Dawley rats after 5 weeks of their birth, both ovaries were extirpated together with the oviducts from the back of each of 48 rats in the sixty rats under anesthesia by pentobarbital (the operation being referred to as OVX). From after one week of the operation, the 48 rats were divided into 4 groups and each rat of the first group was administered with triglyceride of C$_8$ to C$_{10}$-fatty acid (the triglyceride being prepared by Nihon Yushi Co., Ltd. under the registered trade name of PANASATE - 810, hereinafter referred to as MCT) every day for 6 months. Each rat of the second, third and fourth groups was administered with a solution of 24R,25-(OH)$_2$-D$_3$ in MCT at the respective dose rates shown in the following table in the same manner as above.

The remaining twelve rats forming the fifth group were subjected to a false operation (referred hereinafter to as SHAM) and then administered with the triglyceride in the same manner as above as the control group.

TABLE

| Group | Operation | Administration | Dose rate |
|---|---|---|---|
| 1 | OVX | MCT only | — |
| 2 | OVX | 24R,25-(OH)$_2$—D$_3$ in MCT | 1 microgram/kg |
| 3 | OVX | 24R,25-(OH)$_2$—D$_3$ in MCT | 10 microgram/kg |
| 4 | OVX | 24R,25-(OH)$_2$—D$_3$ in MCT | 100 microgram/kg |
| 5 (Control) | SHAM | MCT only | — |

Before 20 days and 10 days before butchering, oxytetracycline was intraperitoneally administered to some rats of each group at a dose rate of 15 mg/kg/time (in total, 2 times), and after butchering the rats, the right tibia was taken from each rat and after fixing the tibia with aqueous 70% by weight ethanolic solution, a specimen was made by imbedding the fixed tibia in a polyester resin (Ligorac) and cutting transversally at the position 10 mm from one end thereof. The distance between the two marks made by oxytetracycline on the specimen, which was determined under a fluorescent microscope was divided by the time period between the two administrations of tetracycline, thereby finding the velocity of osteogenesis (formation of bone) per unit time, the results being shown in Table 1.

Figure 2:
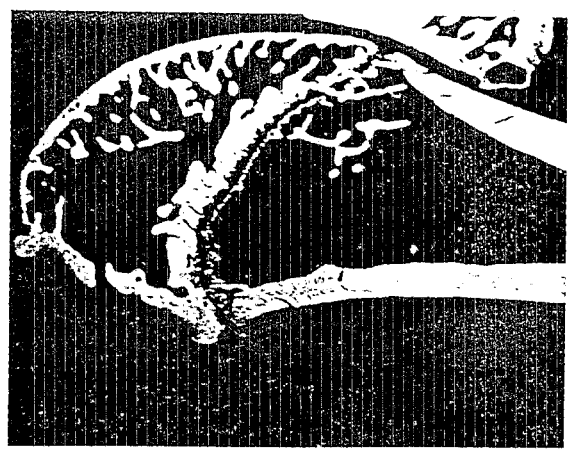
FIG. 2 is that of a rat in the first group (ovaries were extirpated and only MCT was administered) and FIG. 3 is that of a rat in the second group (ovaries were extirpated and 24R,25-$(OH)_2$-$D_3$ in MCT was administered at a dose rate of 1 microgram/kg).
Figure 3:
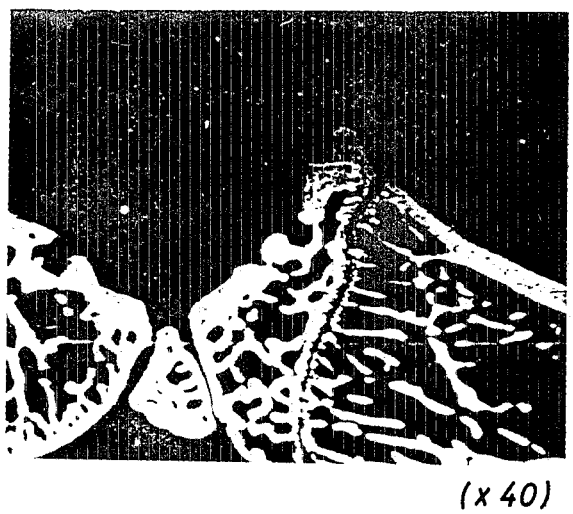

After finishing the administration, all rats were butchered and after collecting the right tibia from each of the butchered animals and preparing the specimen of the tibia following the above-mentioned technique, each of the thus prepared specimens were vertically sliced at the position of 60 to 70 micrometers from one end thereof following the conventional method, and the sliced specimen was subjected to contact microradiography, to carry out the morphological evaluation of the tibia, the results being shown in FIGS. 1 to 3. From FIGS. 1 to 3, it is clearly understood that the osteotrabecule which has once disappeared by OVX was restored in the rat of the group to which the present substance was administered at a dose rate of 1 microgram/kg.

In addition, the right tibia was taken from the butchered rat and defatted by immersing the tibia in acetone, and after drying for 2 days at 110° C., the defatted and dried weight of the right tibia was determined. Thereafter, the tibia was calcined in a porcelain crucible for 5 hours at 900° C., and after dissolving the thus obtained ash of the tibia into aqueous 6N hydrogen chloride solution, the concentration of calcium in the solution was determined following the OCPC method, the results being shown in Table 2.

TABLE 1

| Group | Velocity of osteogenesis (micrometer/day)[1] |
|---|---|
| 1 | 1.11 ± 0.34 |
| 2 | 1.43 ± 0.42 |
| 3 | 1.63 ± 0.38 |
| 4 | 1.92 ± 0.28 |
| 5 | 2.10 ± 0.36 |

Note:
[1]$\overline{X}$ ± S.D.

TABLE 2

| Group | Content of calcium in dried bone (%) |
|---|---|
| 1 | 19.9 ± 0.5 |
| 2 | 20.9 ± 0.3 |
| 3 | 22.2 ± 0.6 |
| 4 | 22.8 ± 0.4 |
| 5 | 23.5 ± 0.4 |

EXAMPLE 2

Biological effects of the present substance

A solution of 24R,25-(OH)$_2$-D$_3$ in triglyceride of C$_8$ to C$_{10}$-fatty acid containing 1% by weight of ethanol was forcibly and orally administered to each of ten male ICR mice or each of ten female ICR mice every day for 30 days at a daily dose rate of 10, 100 or 1000 micrograms/kg, and the results of examination of the physiological conditions were compared to those of the mice administered only with the solvent.

The results of comparison are shown below.

According to the growth curve prepared by weighing the body weight of each mouse during the test period, no significant difference of body weight change was observed between any two groups.

TABLE 3

Test result of general examination of blood

| Group | Sex | Dose rate (μg/kg) | Number of Erythrocyte | Leukocyte | Hemoglobin | Hematocrit value |
|---|---|---|---|---|---|---|
| 2 | male | 10 | none[1] | none | none | none |
| 3 | male | 100 | none | none | none | none |
| 4 | male | 1000 | none | none | none | none |
| 2 | female | 10 | none | none | none | none |
| 3 | female | 100 | none | none | none | none |
| 4 | female | 1000 | none | none | none | none |

Note:
[1]none: means that no difference was found between the group administered with the present substance and the group subjected to false operation and administered only with the solvent.

TABLE 4

Test results of blood biochemical examination

| Group | Sex | Dose rate (μg/kg) | GOT | GPT | LDH | Ca | I-P | ALP | T-P | A/G | Alb | T-Bil | Glu | T-CHO | BUN |
|---|---|---|---|---|---|---|---|---|---|---|---|---|---|---|---|
| 2 | male | 10 | n[1] | n | n | n | n | n | n | n | n | n | n | n | n |
| 3 | male | 100 | n | n | n | n | n | n | n | n | n | n | n | n | n |
| 4 | male | 1000 | n | n | r[2] | n | n | n | n | n | n | r | r | n | r |
| 2 | female | 10 | n | n | n | n | n | n | n | n | n | n | n | n | n |
| 3 | female | 100 | n | n | n | n | n | n | n | n | n | n | n | n | n |
| 4 | female | 1000 | n | n | n | n | n | n | n | n | n | n | n | n | n |

Notes:
[1]"n" means that no difference was observed between the group administered with the present substance and the group subjected to false operation and administered only with MCT.
[2]"r" means that the level of the group administered with the present substance is lower than that of the group subjected to false operation and administered only with MCT.

TABLE 5

Test results of urinalysis

| Group | Sex | Dose rate (μg/kg) | pH | Sugar | Protein | occult blood | Ketone body | urobilinogen |
|---|---|---|---|---|---|---|---|---|
| 2 | male | 10 | n[1] | n | n | n | n | n |
| 3 | male | 100 | n | n | n | n | n | n |
| 4 | male | 1000 | n | n | n | n | n | n |
| 2 | female | 10 | n | n | n | n | n | n |
| 3 | female | 100 | n | n | n | n | n | n |
| 4 | female | 1000 | n | n | n | n | n | n |

Note:
[1]"n" means that no difference was observed between the group administered with the present substance and the group subjected to false operation and administered only with MCT.

TABLE 6

Weight of internal organs

| Group | Sex | Dose rate (μg/kg) | B | P | H | L | Li | S | K | Ad | Th | T | O | U |
|---|---|---|---|---|---|---|---|---|---|---|---|---|---|---|
| 2 | male | 10 | n[2] | | n | n | n | n | n | n | n | n | | |
| 3 | male | 100 | n | n | n | n | n | n | n | n | n | n | | |
| 4 | male | 1000 | n | n | n | n | n | n | n | n | n | n | | |
| 2 | female | 10 | n | n | n | n | n | n | n | n | n | | n | n |
| 3 | female | 100 | n | n | n | n | n | n | n | n | n | | n | n |

TABLE 6-continued

| | | | Weight of internal organs | | | | | | | | | | |
|---|---|---|---|---|---|---|---|---|---|---|---|---|---|
| | | | Organ[1] | | | | | | | | | | |
| Group | Sex | Dose rate (μg/kg) | B | P | H | L | Li | S | K | Ad | Th | T | O | U |
| 4 | female | 1000 | n | n | n | n | n | n | n | n | n | | n | n |

Notes:
[1]Name of organs: B: brain, P: pituitary, H: heart, L: lung, Li: liver, S: spleen, K: kidneys, Ad: adrenal, Th: thymus, T: testes, O: ovaries and U: uterus
[2]"n" means the same as in the table 5.

The following internal organs and tissues taken out of each of the mice were fixed with an aqueous 10% formaldehyde solution and then stained with hematoxylin-.eosin to be subjected to histopathological examination. No abnormal findings were obtained.

The organs and tissues examined were Brain, Heart, Lungs, Liver, Kidneys, Adrenal, Spleen, Pancreas, Thyroid gland, Pituitary, Mesenteric limphnodes, Testes, Ovaries, Uterus, Stomach, Small intestine (jejunum, ileum and duodenum), Large intestine (colon and caecum), Eyeballs, Submaxillary gland, Urinary bladder, Skin on the back, Muscles, Sternum, Bone marrow of sternum and femur and Femur.

EXAMPLE 3

Preparation of soft capsule

Into 1 kg of triglyceride of $C_8$ to $C_{10}$-fatty acid which had been exposed to ultraviolet light from a 400 W high pressure mercury lamp while bubbling argon thereinto, thereby eliminating the impure reactive peroxide therein, 5 mg of 24R,25-$(OH)_2$-$D_3$ was dissolved, and into the thus obtained solution, the following components for wall membrane of capsules were dissolved so as to make one capsule containing 0.5 microgram of 24R,25-$(OH)_2$-$D_3$, and the thus prepared solution was subjected to a soft capsule-forming machine by a conventional method to obtain soft capsules.

Recipe for wall membrane of soft capsule:
10 parts of gelatin,
2 parts of glycerol,
0.05 part of an antiseptic (ethyl p-oxybenzoate),
0.2 part of titanium white and
0.2 part of water In the same manner, capsules respectively containing 1, 2, 5 and 10 micrograms were prepared.

What is claimed is:

1. A method for the treatment of osteoporosis, which comprises administering to a patient suffering from osteoporosis an effective amount of a compound of 24,25-dihydroxycholecalciferol.

2. A method according to claim 1, wherein the compound is 24R,25-dihydroxycholecalciferol.

* * * * *